United States Patent
Chen et al.

(10) Patent No.: US 6,291,614 B1
(45) Date of Patent: Sep. 18, 2001

(54) DINUCLEAR FLUOROARYL ALUMINUM ALKYL COMPLEXES

(75) Inventors: Eugene Y. Chen, Midland; William J. Kruper, Jr., Sanford, both of MI (US)

(73) Assignee: The Dow Chemical Company, Midland, MI (US)

(*) Notice: Subject to any disclaimer, the term of this patent is extended or adjusted under 35 U.S.C. 154(b) by 0 days.

(21) Appl. No.: 09/371,888

(22) Filed: Aug. 9, 1999

Related U.S. Application Data
(60) Provisional application No. 60/100,489, filed on Sep. 16, 1998.

(51) Int. Cl.⁷ .................................................. C08F 4/42
(52) U.S. Cl. .................. 526/151; 526/160; 526/161; 526/159; 526/348; 526/943; 502/103; 502/152; 502/123; 556/170; 556/187
(58) Field of Search ................................ 526/160, 161, 526/159, 151, 348, 943; 502/103, 152, 123; 556/170, 187

(56) References Cited
U.S. PATENT DOCUMENTS

| | | |
|---|---|---|
| 5,453,410 | 9/1995 | Kolthammer et al. . |
| 5,470,993 | 11/1995 | Devore et al. . |
| 5,527,929 | 6/1996 | Timmers et al. . |
| 5,556,928 | 9/1996 | Devore et al. . |
| 5,602,269 * | 2/1997 | Biagini et al. ............ 556/170 |
| 5,616,664 | 4/1997 | Timmers et al. . |
| 5,624,878 | 4/1997 | Devore et al. . |

FOREIGN PATENT DOCUMENTS
520732    12/1995    (EP) .

OTHER PUBLICATIONS
Reddy et al., *Prog. Poly Sci.*, 20, 309–367, (1995).
Marks et al., *J. Am. Chem. Soc.*, 118, 12451–12452, (1996).
Chen et al., *J. Am. Chem. Soc.*, 119, 2582–2583, (1997).
Jia et al., *Organometallics*, 16, 842–857, (1997).
Coles et al., *J. Am. Chem. Soc.*, 119, p. 8126, (1997).
Ewen, *Stud. In Surf. Sci. Catal.*, 89, 405–410, (1994).

* cited by examiner

*Primary Examiner*—David W. Wu
*Assistant Examiner*—Ling-Siu Choi

(57) ABSTRACT

A catalyst activator particularly adapted for use in the activation of metal complexes of metals of Group 3–10 for polymerization of ethylenically unsaturated polymerizable monomers, especially olefins, comprising:

a compound corresponding to the formula:

$$Ar^f_z Al_2 Q^1_{6-z}$$

where;

$Q^1$ independently each occurrence is selected from $C_{1-20}$ alkyl;

$Ar^f$ is a fluorinated aromatic hydrocarbyl moiety of from 6 to 30 carbon atoms;

z is a number greater than 0 and less than 6, and the moiety: $Ar^f_z Al_2 Q^1_{6-z}$ is an adduct of tri (fluoroarylaluminum) with from a sub-stoichiometric to a super-stoichiometric amount of a trialkylaluminum having from 1 to 20 carbons in each alkyl group.

19 Claims, No Drawings

DINUCLEAR FLUOROARYL ALUMINUM ALKYL COMPLEXES

CROSS-REFERENCE TO RELATED APPLICATION

This application claims benefit for priority from provisional application number 60/100,489, filed Sep. 16, 1998.

BACKGROUND OF THE INVENTION

The present invention relates to compounds that are useful as catalyst activator components. More particularly the present invention relates to such compounds that are particularly adapted for use in the coordination polymerization of unsaturated compounds having improved activation efficiency and performance. Such compounds are particularly advantageous for use in a polymerization process wherein catalyst, catalyst activator, and at least one polymerizable monomer are combined under polymerization conditions to form a polymeric product.

It is previously known in the art to activate Ziegler-Natta polymerization catalysts, particularly such catalysts comprising Group 3–10 metal complexes containing delocalized π-bonded ligand groups, by the use of an activator. Generally in the absence of such an activator compound, also referred to as a cocatalyst, little or no polymerization activity is observed. A class of suitable activators are aluminoxanes, or alkylaluminoxanes, which are generally believed to be oligomeric or polymeric alkylaluminoxy compounds, including cyclic oligomers. Generally such compounds contain, on average about 1.5 alkyl groups per aluminum atom, and are prepared by reaction of trialkylaluminum compounds or mixtures of compounds with water (Reddy et al, *Prog. Poly. Sci.*, 1995, 20, 309–367). The resulting product is in fact a mixture of various substituted aluminum compounds including especially, trialklyaluminum compounds (resulting from incomplete reaction of the trialkylaluminum starting reagent or decomposition of the alumoxane). The amount of such free trialkylaluminum compound in the mixture generally varies from 1 to 50 percent by weight of the total product. Examples of alumoxanes include methylalumoxane (MAO) made by hydrolysis of trimethylaluminum as well as modified methylalumoxane (MMAO), made by hydrolysis of a mixture of trimethylaluminum and triisobutylaluminum. MMAO advantageously is more soluble in aliphatic solvents than is MAO.

A different type of activator compound is a Bronsted acid salt capable of transferring a proton to form a cationic derivative or other catalytically active derivative of such Group 3–10 metal complex. Preferred Bronsted acid salts are such compounds containing a cation/anion pair that is capable of rendering the Group 3–10 metal complex catalytically active. Suitable activators comprise fluorinated arylborate anions, most preferably, the tetrakis (pentafluorophenyl)borate anion. Additional suitable anions include sterically shielded diboron anions of the formula:

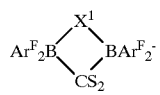

wherein:

S is hydrogen, alkyl, fluoroalkyl, aryl, or fluoroaryl, $Ar^F$ is fluoroaryl, and $X^1$ is either hydrogen or halide, disclosed in U.S. Pat. No. 5,447,895.

Examples of preferred charge separated (cation/anion pair) activators are protonated ammonium, sulfonium, or phosphonium salts capable of transferring a hydrogen ion, disclosed in U.S. Pat. Nos. 5,198,401, 5,132,380, 5,470,927, and 5,153,157, as well as oxidizing salts such as carbonium, ferrocenium and silyilium salts, disclosed in U.S. Pat. Nos. 5,350,723, 5,189,192 and 5,626,087.

Further suitable activators for the above metal complexes include strong Lewis acids including (trisperfluorophenyl) borane and trs(perfluorobiphenyl)borane. The former composition has been previously disclosed for the above stated end use in EP-A-520,732, and elsewhere, whereas the latter composition is disclosed in Marks, et al., *J. Am. Chem. Soc.*, 118, 12451–12452 (1996). Additional teachings of the foregoing activators may be found in Chen, et al, *J. Am. Chem. Soc.* 1997, 119, 2582–2583, Jia et al, *Organometallics*, 1997, 16, 842–857. and Coles et al, *J. Am. Chem. Soc.* 1997, 119, 8126–8126. All of the foregoing salt and Lewis acid activators in practice are based on perfluorophenyl substituted boron compounds. Although the quantity of such activator compound used is quite low, residual boron and fluorinated benzene values remaining in the polymer may be detrimental to final polymer properties, such as applications requiring high dielectrical properties.

In U.S. Pat. No. 5,453,410, an alumoxane, particularly methylalumoxane, was disclosed for use in combination with constrained geometry, Group 4 metal complexes, especially in a molar ratio of metal complex to alumoxane of from 1/1 to 1/50. This combination beneficially resulted in improved polymerization efficiency. Similarly, in U.S. Pat. Nos. 5,527,929, 5,616,664, 5,470,993, 5,556,928, 5,624,878, various combinations of metal complexes with trispentafluorophenyl boron cocatalyst, and optionally an alumoxane, were disclosed for use as catalyst compositions for olefin polymerization.

Despite the satisfactory performance of the foregoing catalyst activators under a variety of polymerization conditions, there is still a need for improved cocatalysts for use in the activation of various metal complexes under a variety of reaction conditions. In particular, it is desirable to remove boron containing contaminating compounds from such activator composition. Such boron containing contaminating compounds result primarily from ligand exchange with the alumoxane, and comprise trialkylboron compounds having from 1 to 4 carbons in each alkyl group, for example, trimethylboron, triisobutylboron, or mixed trialkylboron products. It would be desirable if there were provided compounds that could be employed in solution, slurry, gas phase or high pressure polymerizations and under homogeneous or heterogeneous process conditions having improved activation properties, that lack such trialkylboron species.

It is known that an exchange reaction between aluminum trialkyl compounds and tris(perfluorophenyl)borane occurs under certain conditions. This phenomenon has been previously described in U.S. Pat. No. 5,602,269. Tris (perfluorophenyl)aluminum is a strong Lewis acid as well. However, it generally performs poorly by itself as an activator compared with trs(perfluorophenyl)borane. Similarly, It has further been demonstrated that active catalysts resulting from the use of an aluminate anion based upon tris (perfluorophenyl)aluminum for the activation of ansa-metallocenes and biscyclopentadienyl derivatives of zirconium(IV) are generally of lower activity than those formed by the corresponding borane (Ewen, *Stud. in Surf. Sci. Catal.* 1994, 89, 405–410). The foregoing tri(fluoroaryl) aluminum compounds are considered to be moderately shock and temperature sensitive and difficult to handle in the pure state. In order to avoid this problem, the compounds may be prepared as adducts with Lewis bases such as ethers. Disadvantageously, however, the presence of an ether detrimentally affects the ability to use the compounds as activators for metal complexes, whereas, removing the ether can result in detonation of the compound.

SUMMARY OF THE INVENTION

According to the present invention there is now provided a compound corresponding to the formula:

$$Ar^f_z Al_2 Q^1_{6-z}$$

where;

Q$^1$ independently each occurrence is selected from C$_{1-20}$ alkyl;

Ar$^f$ is a fluorinated aromatic hydrocarbyl moiety of from 6 to 30 carbon atoms;

z is a number greater than 0 and less than 6; and the moiety: $Ar^f_z Al_2 Q^1_{6-z}$, is an adduct of tri(fluoroarylaluminum) with from a sub-stoichiometric to a super-stoichiometric amount of a tralkylaluminum having from 1 to 20 carbons in each alkyl group.

In addition there is provided a process for preparing a compound corresponding to the formula:

$$Ar^f_z Al_2 Q^1_{6-z}$$

where;

Q$^1$ independently each occurrence is selected from C$_{1-20}$ alkyl;

Ar$^f$ is a fluorinated aromatic hydrocarbyl moiety of from 6 to 30 carbon atoms;

z is a number greater than 0 and less than 6; and the moiety: $Ar^f_z Al_2 Q^1_{6-z}$, is an adduct of tri(fluoroarylaluminum) with from a sub-stoichiometric to a super-stoichiometric amount of a trialkylaluminum having from 1 to 20 carbons in each alkyl group, said process comprising contacting:
A) a compound of the formula Ar$^f_3$Me, with
B) a compound of the formula AlQ$^1_3$, wherein Me is aluminum; Ar$^f$, and Q$^1$ are as previously defined, in a molar ratio A:B from 1:0.1 to 1:10, preferably from 1:0.2 to 1:1, most preferably from 1:0.2 to 1:0.5 and at a temperature from −50 to 200° C., preferably 0–60° C., most preferably 20–50° C.; or wherein Me is boron, and Ar$^f$, and Q$^1$ are as previously defined, contacting A) and B) in a molar ratio A:B from 1:1.1 to 1:10, preferably from 1:1.2 to 1:6, at a temperature from 20 to 60° C., more preferably 25 to 50° C.

The moieties (Ar$^f_z$Al$_2$Q$^1_{6-z}$) may exist as discrete entities or dynamic exchange products. That is, such moieties may be in the form of dimeric products as written or in the form of multi-centered products in combination with metal complexes and other organometallic compounds, including those resulting from partial or complete ligand exchange during the process used for their manufacture. Such more complex mixture of compounds may result from a combination of the foregoing compounds, which are Lewis acid adducts, with other compounds such as metallocenes or alumoxanes. Such exchange products may be fluxional in nature, the concentration thereof being dependant on time, temperature, solution concentration and the presence of other species able to stabilize the compounds, thereby preventing or slowing further ligand exchange. Preferably z is from 1–5, more preferably from 4–5.

Surprisingly, the foregoing compounds are highly active cocatalysts for use in combination with Group 4 metal complexes as olefin polymerization catalyst compositions. In particular, the compositions of the invention are highly desirable for use in polymerization processes in combination with Group 4 metal complexes containing one or two cyclopentadienyl groups (including substituted, multiple ring and partially hydrogenated cyclopentadienyl derivatives).

When used as a co-catalyst for use in activation of metal complexes, especially Group 4 metallocenes for the polymerization of olefins, it is desirable to employ the compounds in a dilute concentration in, for example, a hydrocarbon liquid, especially an aliphatic hydrocarbon liquid, for use in a homogeneous, especially, solution polymerization. Additionally, the compositions may be deposited on an inert support, especially a particulated metal oxide or polymer, in combination with the metal complex to be activated according to known techniques for use in a gas phase, powder bed or slurry polymerization.

Additionally according to the present invention there is
provided a catalyst composition for polymerization of an ethylenically unsaturated, polymerizable monomer comprising, in combination, the above described composition and a Group 3–10 metal complex, or the reaction product resulting from such combination.

Even further according to the present invention there is
provided a process for polymerization of one or more addition polymerizable monomers comprising contacting the same, optionally in the presence of an inert aliphatic, alicyclic or aromatic hydrocarbon, with the above catalyst composition or a supported derivative thereof.

DETAILED DESCRIPTION

All references herein to elements belonging to a certain Group refer to the Periodic Table of the Elements published and copyrighted by CRC Press, Inc., 1995. Also any reference to the Group or Groups shall be to the Group or Groups as reflected in this Periodic Table of the Elements using the IUPAC system for numbering groups. Where any reference is made herein to any publication, patent application or provisional patent application, the contents thereof are incorporated herein in its entirety by reference.

Preferred compositions according to the present invention
are those wherein Ar$^f$ is perfluoroaryl, and Q$^1$ is C$_{1-4}$ alkyl. Most preferred compositions according to the present invention are those wherein Ar is pentafluorophenyl, and Q$^1$ each occurrence is methyl, isopropyl or isobutyl.

The skilled artisan will appreciate that various adducts
and mixtures of adducts may be produced in the reactions contemplated herein. Moreover, the present invented product is not necessarily a single compound, nor must it be separated from reaction by-products or additional exchange products in order to be useful or within the present invention. Examples of the various reaction products and dynamic exchange products that result and have been identified in the manufacture of the present invented compounds are illustrated in the following chart:

1. $Ar^f_3Al + Q^1_3Al \rightarrow Ar^f_3Al_2Q^1_3 = (Ar^f_3Al.AlQ^1_3)$
2. $Ar^f_3B + 2Q^1_3Al \rightarrow BQ^1_3 + Ar^f_3Al_2Q^1_3 = (Ar^f_3Al.AlQ^1_3)$
3. $Ar^f_3Al + 2Q^1_3Al \rightarrow 3Ar^fAlQ^1_2 \rightarrow 3/2\ Ar^f_2Al_2Q^1_4 = (Ar^f_3Al.2AlQ^1_3)$
4. $Ar^f_3Al + 3Q^1_3Al \rightarrow Ar^f_2Al_2Q^1_4 + Ar^fAl_2Q^1_5 = (Ar^f_3Al.3AlQ^1_3)$ 7. $5Ar^f_3B + 6Q^1_3Al \rightarrow 5\ BQ^1_3 + Ar^f_5Al_2Q^1 = (Ar^f_3Al \cdot \frac{1}{3}AlQ^1_3)$ The compositions of the invention are readily prepared by combining the tri(fluoroaryl)aluminum compound and trialkylaluminum compound. The reaction may be performed in a solvent or diluent, or neat. Intimate contacting of the neat reactants can be effectively achieved by drying a solution of the two reactants to form a solid mixture, and thereafter optionally continuing such contacting, optionally at an elevated temperature. Preferred tri(fluoroaryl) aluminum compounds are tris(perfluoroaryl)aluminum compounds, most preferably tris(pentafluorophenyl) aluminum. The latter compound may be readily prepared by ligand exchange of a trifluoroarylboron compound and a trialkylaluminum compound, especially trimethyl aluminum.

Alternatively, the compositions of the present invention may be prepared by reacting a tri(fluoroaryl)boron compound directly with greater than a stoichiometric amount of a trialkyl aluminum compound, optionally followed by removal of alkylboron intermediate products. By using a ratio of tri(fluoroaryl)boron compound to trialkyl aluminum compound greater than stoichiometric, particularly a molar ratio from 1:1.1 to 1:10, especially from 1:1.2 to 1:6, and additionally, by continuing the reaction for relatively long periods of time, preferably at least one hour at a temperature from 20 to 60° C., more preferably at least 2 hours at a temperature of 25 to 50° C., the compositions of the invention may be readily prepared in high efficiency.

Either of the foregoing reactions may be performed in any aliphatic, alicyclic or aromatic liquid diluent or mixture thereof. Preferred are $C_{6-8}$ aliphatic and alicyclic hydrocarbons and mixtures thereof, including hexane, heptane, cyclohexane, and mixed fractions such as Isopar™ E, available from Exxon Chemicals Inc. More preferably however, the reactants are reacted in the absence of a diluent, that is, the neat reactants are merely combined and heated. Solutions of the two reactants may be utilized, followed by liquid removal in order to obtain an intimate mixture prior to heating the same. Desirably, the contacting is also done prior to addition of a metal complex catalyst, such as a metallocene, in order to avoid formation of further derivatives and multiple metal exchange products having reduced catalytic effectiveness. After contacting the reaction mixture may be purified to remove ligand exchange products, especially any trialkylboron compounds by any suitable technique. Alternatively, but less desirably, a Group 3-10 metal complex catalyst may first be combined with the reaction mixture prior to removing the residual ligand exchange products.

Suitable techniques for removing alkyl exchange byproducts from the reaction mixture include degassing optionally at reduced pressures, distillation, solvent exchange, solvent extraction, extraction with a volatile agent, contacting with a zeolite or molecular sieve, and combinations of the foregoing techniques, all of which are conducted according to conventional procedures. Preferably the quantity of residual trialkylboron exchange product is less than 10 mole percent, more preferably less than 1.0 mole percent, most preferably less than 0.1 mole percent, based on aluminum metal content. Highly preferred compounds according to the invention are those comprising less than one tri(alkyl) aluminum moiety per tri(fluoroaryl)aluminum moiety. Most highly desired adducts are those corresponding to the formula: $Ar^f_4Al_2Q^1_2$ and $Ar^f_5Al_2Q^1$. Such compositions possess extremely high catalyst activation properties.

When in use as a catalyst activator, the molar ratio of metal complex to activator composition is preferably from 0.1:1 to 3:1, more preferably from 0.2:1 to 2:1, most preferably from 0.25:1 to 1:1, based on the metal contents of each component. In most polymerization reactions the molar ratio of metal complex: polymerizable compound employed is from $10^{-12}:1$ to $10^{-1}:1$, more preferably from $10^{-12}:1$ to $10^{-5}:1$.

The reagents employed in the preparation and use of the present compounds and catalyst compositions, should be thoroughly dried and deareated prior to use, and handled under high vacuum or inert reaction conditions. Solid components such as metal oxide supports are preferably dried by heating at 200–500° C., optionally under reduced pressure, for a time from 10 minutes to 100 hours prior to use.

The support when the activator component is used as a supported catalyst component, may be any inert, particulate material, but most suitably is a metal oxide or mixture of metal oxides, preferably alumina, silica, an aluminosilicate or clay material. Suitable volume average particle sizes of the support are from 1 to 1000 μM, preferably from 10 to 100 μM. Most desired supports are calcined silica, which may be treated prior to use to reduce surface hydroxyl groups thereon, by reaction with a silane, a trialkylaluminum, or similar reactive compound. Any suitable means for incorporating the present composition onto the surface of a support (including the interstices thereof) may be used, including dispersing the co-catalyst in a liquid and contacting the same with the support by slurrying, impregnating, spraying, or coating and thereafter removing the liquid, or by combining the cocatalyst and a support material in dry or paste form and intimately contacting the mixture, thereafter forming a dried, particulated product.

Suitable metal complexes for use in combination with the foregoing cocatalysts include any complex of a metal of Groups 3-10 of the Periodic Table of the Elements capable of being activated to polymerize addition polymerizable compounds, especially olefins by the present activators. Examples include Group 10 diamine derivatives corresponding to the formula:

M* is Ni(II) or Pd(II);

X' is halo, hydrocarbyl, or hydrocarbyloxy;

Ar* is an aryl group, especially 2,6-diisopropylphenyl or aniline group;

CT-CT is 1,2-ethanediyl, 2,3-butanediyl, or form a fused ring system wherein the two T groups together are a 1,8-naphthanediyl group; and A⁻ is the anionic component of the foregoing charge separated activators.

Similar complexes to the foregoing are also disclosed by M. Brookhart, et al., in J. Am. Chem. Soc., 118, 267–268 (1996) and J. Am. Chem. Soc., 117, 6414 –6415 (1995), as being active polymerization catalysts especially for polymerization of α-olefins, either alone or in combination with polar comonomers such as vinyl chloride, alkyl acrylates and alkyl methacrylates.

Additional complexes include derivatives of Group 3,4, or Lanthanide metals containing from 1 to 3 π-bonded anionic or neutral ligand groups, which may be cyclic or non-cyclic delocalized π-bonded anionic ligand groups. Exemplary of such π-bonded anionic ligand groups are conjugated or nonconjugated, cyclic or non-cyclic dienyl groups, allyl groups, boratabenzene groups, and arene groups. By the term "π-bonded" is meant that the ligand group is bonded to the transition metal by a sharing of electrons from a partially delocalized π-bond.

Each atom in the delocalized π-bonded group may independently be substituted with a radical selected from the group consisting of hydrogen, halogen, hydrocarbyl, halohydrocarbyl, hydrocarbyl-substituted metalloid radicals wherein the metalloid is selected from Group 14 of the Periodic Table of the Elements, and such hydrocarbyl- or hydrocarbyl-substituted metalloid radicals further substituted with a Group 15 or 16 hetero atom containing moiety. Included within the term "hydrocarbyl" are $C_{1-20}$ straight, branched and cyclic alkyl radicals, $C_{6-20}$ aromatic radicals, $C_{7-20}$ alkyl-substituted aromatic radicals, and $C_{7-20}$ aryl-substituted alkyl radicals. In addition two or more such radicals may together form a fused ring system, including partially or fully hydrogenated fused ring systems, or they may form a metallocycle with the metal. Suitable hydrocarbyl-substituted organometalloid radicals include mono-, di- and tri-substituted organometalloid radicals of Group 14 elements wherein each of the hydrocarbyl groups contains from 1 to 20 carbon atoms. Examples of suitable hydrocarbyl-substituted organometalloid radicals include trimethylsilyl, triethylsilyl, ethyldimethylsilyl, methyidiethylsilyl, triphenylgermyl, and trimethylgermyl groups. Examples of Group 15 or 16 hetero atom containing moieties include amine, phosphine, ether or thioether moieties or divalent derivatives thereof, e. g. amide, phosphide, ether or thioether groups bonded to the transition metal or Lanthanide metal, and bonded to the hydrocarbyl group or to the hydrocarbyl-substituted metalloid containing group.

Examples of suitable anionic, delocalized π-bonded groups include cyclopentadienyl, indenyl, fluorenyl, tetrahydroindenyl, tetrahydrofluorenyl, octahydrofluorenyl, pentadienyl, cyclohexadienyl, dihydroanthracenyl, hexahydroanthracenyl, decahydroanthracenyl groups, and boratabenzene groups, as well as $C_{1-10}$ hydrocarbyl-substituted or $C_{1-10}$ hydrocarbyl-substituted silyl substituted derivatives thereof. Preferred anionic delocalized π-bonded groups are cyclopentadienyl, pentamethylcyclopentadienyl, tetramethylcyclopentadienyl, tetramethylsilylcyclopentadienyl, indenyl, 2,3-dimethylindenyl, fluorenyl, 2-methylindenyl, 2-methyl-4-phenylindenyl, tetrahydrofluorenyl, octahydrofluorenyl, and tetrahydroindenyl.

The boratabenzenes are anionic ligands which are boron containing analogues to benzene. They are previously known in the art having been described by G. Herberich, et al., in *Organometallics*, 1995, 14, 1, 471–480. Preferred boratabenzenes correspond to the formula:

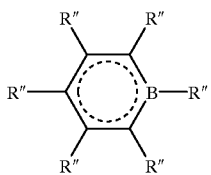

wherein R" is selected from the group consisting of hydrocarbyl, silyl, or germyl, said R" having up to 20 non-hydrogen atoms. In complexes involving divalent derivatives of such delocalized π-bonded groups one atom thereof is bonded by means of a covalent bond or a covalently bonded divalent group to another atom of the complex thereby forming a bridged system.

Suitable metal complexes for use in the catalysts of the present invention may be derivatives of any transition metal including Lanthanides, but preferably of Group 3, 4, or Lanthanide metals which are in the +2, +3, or +4 formal oxidation state meeting the previously mentioned requirements. Preferred compounds include metal complexes (metallocenes) containing from 1 to 3 π-bonded anionic ligand groups, which may be cyclic or noncyclic delocalized π-bonded anionic ligand groups. Exemplary of such π-bonded anionic ligand groups are conjugated or nonconjugated, cyclic or non-cyclic dienyl groups, allyl groups, and arene groups. By the term "π-bonded" is meant that the ligand group is bonded to the transition metal by means of delocalized electrons present in a π bond.

Each atom in the delocalized π-bonded group may independently be substituted with a radical selected from the group consisting of halogen, hydrocarbyl, halohydrocarbyl, and hydrocarbyl-substituted metalloid radicals wherein the metalloid is selected from Group 14 of the Periodic Table of the Elements. Included within the term "hydrocarbyl" are $C_{1-20}$ straight, branched and cyclic alkyl radicals, $C_{6-20}$ aromatic radicals, $C_{7-20}$ alkyl-substituted aromatic radicals, and $C_{7-20}$ aryl-substituted alkyl radicals. In addition two or more such radicals may together form a fused ring system or a hydrogenated fused ring system. Suitable hydrocarbyl-substituted organometalloid radicals include mono-, di- and trisubstituted organometalloid radicals of Group 14 elements wherein each of the hydrocarbyl groups contains from 1 to 20 carbon atoms. Examples of suitable hydrocarbyl-substituted organometalloid radicals include trimethylsilyl, triethylsilyl, ethyidimethylsilyl, methyldiethylsilyl, triphenylgermyl, and trimethylgermyl groups.

Examples of suitable anionic, delocalized π-bonded groups include cyclopentadienyl, indenyl, fluorenyl, tetrahydroindenyl, tetrahydrofluorenyl, octahydrofluorenyl, pentadienyl, cyclohexadienyl, dihydroanthracenyl, hexahydroanthracenyl, and decahydroanthracenyl groups, as well as $C_{1-10}$ hydrocarbyl-substituted derivatives thereof. Preferred anionic delocalized π-bonded groups are cyclopentadienyl, pentamethylcyclopentadienyl, tetramethylcyclopentadienyl, indenyl, 2,3-dimethylindenyl, fluorenyl, 2-methylindenyl and 2-methyl-4-phenylindenyl.

More preferred are metal complexes corresponding to the formula:

$L_lMX_mX'_nX''_p$, or a dimer thereof wherein:

L is an anionic, delocalized, π-bonded group that is bound to M, containing up to 50 nonhydrogen atoms, optionally two L groups may be joined together through one or more substituents thereby forming a bridged structure, and further optionally one L may be bound to X through one or more substituents of L;

M is a metal of Group 4 of the Periodic Table of the Elements in the +2, +3 or +4 formal oxidation state;

X is an optional, divalent substituent of up to 50 non-hydrogen atoms that together with L forms a metallocycle with M;

X' is an optional neutral Lewis base having up to 20 non-hydrogen atoms;

X" each occurrence is a monovalent, anionic moiety having up to 40 non-hydrogen atoms, optionally, two X" groups may be covalently bound together forming a divalent dianionic moiety having both valences bound to M, or form a neutral, conjugated or nonconjugated diene that is π-bonded to M (whereupon M is in the +2 oxidation state), or further optionally one or more X" and one or more X' groups may be bonded together thereby forming a moiety that is both covalently bound to M and coordinated thereto by means of Lewis base functionality;

l is 1 or 2;

m is 0 or 1;

n is a number from 0 to 3;

p is an integer from 0 to 3; and the sum, l+m+p, is equal to the formal oxidation state of M.

Such preferred complexes include those containing either one or two L groups. The latter complexes include those containing a bridging group linking the two L groups. Preferred bridging groups are those corresponding to the formula $(ER^*_2)_x$ wherein E is silicon or carbon, $R^*$ independently each occurrence is hydrogen or a group selected from silyl, hydrocarbyl, hydrocarbyloxy and combinations thereof, said $R^*$ having up to 30 carbon or silicon atoms, and x is 1 to 8. Preferably, $R^*$ independently each occurrence is methyl, benzyl, tert-butyl or phenyl.

Examples of the foregoing bis(L) containing complexes are compounds corresponding to the formula:

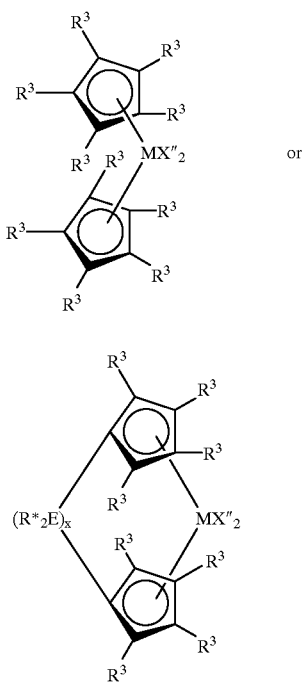

wherein:

M is titanium, zirconium or hafnium, preferably zirconium or hafnium, in the +2 or +4 formal oxidation state;

$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative (that is, a hydrocarbylaryl, siladiyl or germadiyl group) thereby forming a fused ring system, and X" independently each occurrence is an anionic ligand group of up to 40 nonhydrogen atoms, or two X" groups together form a divalent anionic ligand group of up to 40 nonhydrogen atoms or together are a conjugated diene having from 4 to 30 non-hydrogen atoms forming a π-complex with M, whereupon M is in the +2 formal oxidation state, and $R^*$, E and x are as previously defined.

The foregoing metal complexes are especially suited for the preparation of polymers having stereoregular molecular structure. In such capacity it is preferred that the complex possess $C_2$ symmetry or possess a chiral, stereorigid structure. Examples of the first type are compounds possessing different delocalized π-bonded systems, such as one cyclopentadienyl group and one fluorenyl group. Similar systems based on Ti(IV) or Zr(IV) were disclosed for preparation of syndiotactic olefin polymers in Ewen, et al., *J. Am. Chem. Soc.* 110, 6255–6256 (1980). Examples of chiral structures include bis-indenyl complexes. Similar systems based on Ti(IV) or Zr(IV) were disclosed for preparation of isotactic olefin polymers in Wild et al., *J. Organomet. Chem*, 232, 233–47, (1982).

Exemplary bridged ligands containing two π-bonded groups are: (dimethylsilyl-bis-cyclopentadienyl), (dimethylsilyl-bis-methylcyclopentadienyl), (dimethylsilyl-bis-ethylcyclopentadienyl, (dimethylsilyl-bis-t-butylcyclopentadienyl), (dimethylsilyl-bis-tetramethylcyclopentadienyl), (dimethylsilyl-bis-indenyl), (dimethylsilyl-bis-tetrahydroindenyl), (dimethylsilyl-bis-fluorenyl), (dimethylsilyl-bis-tetrahydrofluorenyl), (dimethylsilyl-bis-2-methyl-4-phenylindenyl), (dimethylsilyl-bis-2-methylindenyl), (dimethylsilyl-cyclopentadienyl-fluorenyl), (1,1,2,2-tetramethyl-1,2-disilyl-bis-cyclopentadienyl), (1,2-bis(cyclopentadienyl) ethane, and (isopropylidene-cyclopentadienyl-fluorenyl).

Preferred X" groups are selected from hydride, hydrocarbyl, silyl, germyl, halohydrocarbyl, halosilyl, silylhydrocarbyl and aminohydrocarbyl groups, or two X" groups together form a divalent derivative of a conjugated diene or else together they form a neutral, π-bonded, conjugated diene. Most preferred X" groups are $C_{1-20}$ hydrocarbyl groups.

A further class of metal complexes utilized in the present invention correspond to the formula:

$L_lMX_mX'_nX''_p$, or a dimer thereof wherein:

L is an anionic, delocalized, π-bonded group that is bound to M, containing up to 50 nonhydrogen atoms;

M is a metal of Group 4 of the Periodic Table of the Elements in the +2, +3 or +4 formal oxidation state;

X is a divalent substituent of up to 50 non-hydrogen atoms that together with L forms a metallocycle with M;

X' is an optional neutral Lewis base ligand having up to 20 non-hydrogen atoms;

X" each occurrence is a monovalent, anionic moiety having up to 20 non-hydrogen atoms, optionally two X" groups together may form a divalent anionic moiety having both valences bound to M or a neutral $C_{5-30}$ conjugated diene, and further optionally X' and X" may be bonded together thereby forming a moiety that is both covalently bound to M and coordinated thereto by means of Lewis base functionality;

l is 1 or 2;

m is 1;

n is a number from 0 to 3;

p is an integer from 1 to 2; and the sum, l+m+p, is equal to the formal oxidation state of M.

Preferred divalent X substituents preferably include groups containing up to 30 nonhydrogen atoms comprising at least one atom that is oxygen, sulfur, boron or a member of Group 14 of the Periodic Table of the Elements directly attached to the delocalized π-bonded group, and a different atom, selected from the group consisting of nitrogen, phosphorus, oxygen or sulfur that is covalently bonded to M.

A preferred class of such Group 4 metal coordination complexes used according to the present invention correspond to the formula:

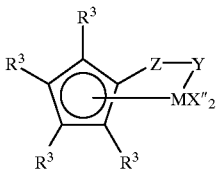

wherein:
M is titanium or zirconium in the +2 or +4 formal oxidation state;
$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative (that is, a hydrocarbylaryl, siladiyl or germadiyl group) thereby forming a fused ring system,
each X" is a halo, hydrocarbyl, hydrocarbyloxy or silyl group, said group having up to 20 nonhydrogen atoms, or two X" groups together form a $C_{5-30}$ conjugated diene;
Y is —O—, —S—, —NR*—, —PR*—; and
Z is $SiR*_2$, $CR*_2$, $SiR*_2SiR*_2$, $CR*_2CR*_2$, $CR*=CR*$, $CR*_2SiR*_2$, or $GeR*_2$,
wherein: R* is as previously defined.

Illustrative Group 4 metal complexes that may be employed in the practice of the present invention include:
cyclopentadienyltitaniumtrimethyl,
cyclopentadienyltitaniumtriethyl,
cyclopentadienyltitaniumtriisopropyl,
cyclopentadienyltitaniumtriphenyl,
cyclopentadienyltitaniumtribenzyl,
cyclopentadienyltitanium-2,4-pentadienyl,
cyclopentadienyltitaniumdimethylmethoxide,
cyclopentadienyltitaniumdimethylchloride,
pentamethylcyclopentadienyltitaniumtrimethyl,
indenyltitaniumtrimethyl,
indenyltitaniumtriethyl,
indenyltitaniumtripropyl,
indenyltitaniumtriphenyl,
tetrahydroindenyltitaniumtribenzyl,
pentamethylcyclopentadienyltitaniumtriisopropyl,
pentamethylcyclopentadienyltitaniumtribenzyl,
pentamethylcyclopentadienyltitaniumdimethylmethoxide,
pentamethylcyclopentadienyltitaniumdimethylchloride,
($\eta^5$-2,4-dimethyl-1,3-pentadienyl)titaniumtrimethyl,
octahydrofluorenyltitaniumtrimethyl,
tetrahydroindenyltitaniumtrimethyl,
tetrahydrofluorenyltitaniumtrimethyl,
(1,1-dimethyl-2,3,4,9,10-$\eta$-1,4,5,6,7,8-hexahydronaphthalenyl)titaniumtrimethyl,
(1,1,2,3-tetramethyl-2,3,4,9,10-$\eta$-1,4,5,6,7,8-hexahydronaphthalenyl)titaniumtrimethyl,
(tert-butylamido)(tetramethyl-$\eta^5$-cyclopentadienyl) dimethylsilanetitanium dichloride,
(tert-butylamido)(tetramethyl-$\eta^5$-cyclopentadienyl) dimethylsilanetitanium dimethyl,
(tert-butylamido)(tetramethyl-$\eta^5$-cyclopentadienyl)-1,2-ethanediyltitanium dimethyl,
(tert-butylamido)(hexamethyl-$\eta^5$-indenyl) dimethylsilanetitanium dimethyl,
(tert-butylamido)(tetramethyl-$\eta^5$-cyclopentadienyl) dimethylsilane titanium (III) 2-(dimethylamino)benzyl;
(tert-butylamido)(tetramethyl-$\eta^5$-cyclopentadienyl) dimethylsilanetitanium (III) allyl,
(tert-butylamido)(tetramethyl-$\eta^5$-cyclopentadienyl) dimethylsilanetitanium (II) 1,4-diphenyl-1,3-butadiene,
(tert-butylamido)(2-methylindenyl)dimethylsilanetitanium (II) 1,4-diphenyl-1,3-butadiene,
(tert-butylamido)(2-methylindenyl)dimethylsilanetitanium (IV) 1,3-butadiene,
(tert-butylamido)(2,3-dimethylindenyl) dimethylsilanetitanium (II) 1,4-diphenyl-1,3-butadiene,
(tert-butylamido)(2,3-dimethylindenyl) dimethylsilanetitanium (IV) 1,3-butadiene,
(tert-butylamido)(2,3-dimethylindenyl) dimethylsilanetitanium (II) 1,3-pentadiene,
(tert-butylamido)(2-methylindenyl)dimethylsilanetitanium (II) 1,3-pentadiene,
(tert-butylamido)(2-methylindenyl)dimethylsilanetitanium (IV) dimethyl,
(tert-butylamido)(2-methyl-4-phenylindenyl) dimethylsilanetitanium (II) 1,4-diphenyl-1,3-butadiene,
(tert-butylamido)(tetramethyl-$\eta^5$-cyclopentadienyl) dimethylsilanetitanium (IV) 1,3-butadiene,
(tert-butylamido)(tetramethyl-$\eta^5$-cyclopentadienyl) dimethylsilanetitanium (II) 1,4-dibenzyl-1,3-butadiene,
(tert-butylamido)(tetramethyl-$\eta^5$-cyclopentadienyl) dimethylsilanetitanium (II) 2,4-hexadiene,
(tert-butylamido)(tetramethyl-$\eta^5$-cyclopentadienyledimethylsilanetitanium (II) 3-methyl 1,3-pentadiene,
(tert-butylamido)(2,4-dimethyl-1,3-pentadien-2-yl) dimethylsilanetitaniumdimethyl,
(tert-butylamido)(1,1-dimethyl-2,3,4,9,10-$\eta$-1,4,5,6,7,8-hexahydronaphthalen-4-yl) dimethylsilanetitaniumdimethyl,
(tert-butylamido)(1,1,2,3-tetramethyl-2,3,4,9,10-$\eta$-1,4,5,6,7,8-hexahydronaphthalen-4-yl) dimethylsilanetitaniumdimethyl,
(tert-butylamido)(tetramethylcyclopentadienyl) dimethylsilanetitanium 1,3-pentadiene,
(tert-butylamido)(3-(N-pyrrolidinyl)inden-1-yl) dimethylsilanetitanium 1,3-pentadiene,
(tert-butylamido)(2-methyl-s-indacen-1-yl) dimethylsilanetitanium 1,3-pentadiene, and
(tert-butylamido)(3,4-cyclopenta(phenanthren-2-yl) dimethylsilanetitanium 1,4-diphenyl-1,3-butadiene.

Bis(L) containing complexes including bridged complexes suitable for use in the present invention include:
biscyclopentadienylzirconiumdimethyl,
biscyclopentadienyltitaniumdiethyl,
biscyclopentadienyltitaniumdiisopropyl,
biscyclopentadienyltitaniumdiphenyl,
biscyclopentadienylzirconium dibenzyl,
biscyclopentadienyltitanium-2,4-pentadienyl,
biscyclopentadienyltitaniummethylmethoxide,
biscyclopentadienyltitaniummethylchloride,
bispentamethylcyclopentadienyltitaniumdimethyl,
bisindenyltitaniumdimethyl,
indenylfluorenyltitaniumdiethyl,
bisindenyltitaniummethyl(2-(dimethylamino)benzyl),
bisindenyltitanium methyltrimethylsilyl,
bistetrahydroindenyltitanium methyltrimethylsilyl,
bispentamethylcyclopentadienyltitaniumdiisopropyl,
bispentamethylcyclopentadienyltitaniumdibenzyl,
bispentamethylcyclopentadienyltitaniummethylmethoxide,
bispentamethylcyclopentadienyltitaniummethylchlodide, (dimethylsilyl-bis-cyclopentadienyl)zirconiumdimethyl,
(dimethylsilyl-bis-pentamethylcyclopentadienyl)titanium-2,
   4-pentadienyl,
(dimethylsilyl-bis-t-butylcyclopentadienyl)
   zirconiumdichloride,
(methylene-bis-pentamethylcyclopentadienyl)titanium(III)
   2-(dimethylamino)benzyl,
(dimethylsilyl-bis-indenyl)zirconiumdichloride,
(dimethylsilyl-bis-2-methylindenyl)zirconiumdimethyl,
(dimethylsilyl-bis-2-methyl-4-phenylindenyl)
   zirconiumdimethyl,
(dimethylsilyl-bis-2-methylindenyl)zirconium-1,4-
   diphenyl-1,3-butadiene,
(dimethylsilyl-bis-2-methyl-4-phenylindenyl)zirconium (II)
   1,4-diphenyl-1,3-butadiene,
(dimethylsilyl-bis-tetrahydroindenyl)zirconium(II) 1,4-
   diphenyl-1,3-butadiene,
(dimethylsilyl-bis-fluorenyl)zirconiumdichloride,
(dimethylsilyl-bis-tetrahydrofluorenyl)zirconiumdi
   (trimethylsilyl),
(isopropylidene)(cyclopentadienyl)(fluorenyl)
   zirconiumdibenzyl, and
(dimethylsilyipentamethylcyclopentadienylfluorenyl)
   zirconiumdimethyl.

Suitable polymerizable monomers include ethylenically unsaturated monomers, acetylenic compounds, conjugated or non-conjugated dienes, and polyenes. Preferred monomers include olefins, for examples alpha-olefins having from 2 to 20,000, preferably from 2 to 20, more preferably from 2 to 8 carbon atoms and combinations of two or more of such alpha-olefins. Particularly suitable alpha-olefins include, for example, ethylene, propylene, 1-butene, 1-pentene, 4-methylpentene-1, 1-hexene, 1-heptene, 1-octene, 1-nonene, 1-decene, 1-undecene, 1-dodecene, 1-tridecene, 1-tetradecene, 1-pentadecene, or combinations thereof, as well as long chain vinyl terminated oligomeric or polymeric reaction products formed during the polymerization, and $C_{10-30}$ α-olefins specifically added to the reaction mixture in order to produce relatively long chain branches in the resulting polymers. Preferably, the alpha-olefins are ethylene, propene, 1-butene, 4-methyl-pentene-1,1-hexene, 1-octene, and combinations of ethylene and/or propene with one or more of such other alpha-olefins. Other preferred monomers include styrene, halo- or alkyl substituted styrenes, tetrafluoroethylene, vinylcyclobutene, 1,4-hexadiene, dicyclopentadiene, ethylidene norbomene, and 1,7-octadiene. Mixtures of the above-mentioned monomers may also be employed.

In general, the polymerization may be accomplished at conditions well known in the prior art for Ziegler-Natta or Kaminsky-Sinn type polymerization reactions. Examples of such well known polymerization processes are depicted in WO 88/02009, U.S. Pat. Nos. 5,084,534, 5,405,922, 4,588,790, 5,032,652, 4,543,399, 4,564,647, 4,522,987, and elsewhere. Preferred polymerization temperatures are from 0–250° C. Preferred polymerization pressures are from atmospheric to 3000 atmospheres.

Molecular weight control agents can be used in combination with the present cocatalysts. Examples of such molecular weight control agents include hydrogen, silanes or other known chain transfer agents. A particular benefit of the use of the present cocatalysts is the ability (depending on reaction conditions) to produce narrow molecular weight distribution α-olefin homopolymers and copolymers in greatly improved cocatalyst efficiencies and purity, especially with respect to residual aluminum containing contaminants. Preferred polymers have Mw/Mn of less than 2.5, more preferably less than 2.3. Such narrow molecular weight distribution polymer products are highly desirable due to improved tensile strength properties.

Gas phase processes for the polymerization of $C_{2-6}$ olefins, especially the homopolymerization and copolymerization of ethylene and propylene, and the copolymerization of ethylene with $C_{3-6}$ α-olefins such as, for example, 1-butene, 1-hexene, 4-methyl-1-pentene are well known in the art. Such processes are used commercially on a large scale for the manufacture of high density polyethylene (HDPE), medium density polyethylene (MDPE), linear low density polyethylene (LLDPE) and polypropylene.

The gas phase process employed can be, for example, of the type which employs a mechanically stirred bed or a gas fluidized bed as the polymerization reaction zone. Preferred is the process wherein the polymerization reaction is carried out in a vertical cylindrical polymerization reactor containing a fluidized bed of polymer particles supported above a perforated plate, the fluidization grid, by a flow of fluidization gas.

The gas employed to fluidize the bed comprises the monomer or monomers to be polymerized, and also serves as a heat exchange medium to remove the heat of reaction from the bed. The hot gases emerge from the top of the reactor, normally via a tranquilization zone, also known as a velocity reduction zone, having a wider diameter than the fluidized bed and wherein fine particles entrained in the gas stream have an opportunity to gravitate back into the bed. It can also be advantageous to use a cyclone to remove ultra-fine particles from the hot gas stream. The gas is then normally recycled to the bed by means of a blower or compressor and a one or more heat exchangers to strip the gas of the heat of polymerization.

A preferred method of cooling of the bed, in addition to the cooling provided by the cooled recycle gas, is to feed a volatile liquid to the bed to provide an evaporative cooling effect. The volatile liquid employed in this case can be, for example, a volatile inert liquid, for example, a saturated hydrocarbon having 3 to 8, preferably 4 to 6, carbon atoms. In the case that the monomer or comonomer itself is a volatile liquid, or can be condensed to provide such a liquid this can be suitably be fed to the bed to provide an evaporative cooling effect. Examples of olefin monomers which can be employed in this manner are olefins containing from 3 to eight, preferably from 3 to six carbon atoms. The volatile liquid evaporates in the hot fluidized bed to form gas which mixes with the fluidizing gas. If the volatile liquid is a monomer or comonomer, it will undergo some polymerization in the bed. The evaporated liquid then emerges from the reactor as part of the hot recycle gas, and enters the compression/heat exchange part of the recycle loop. The recycle gas is cooled in the heat exchanger and, if the temperature to which the gas is cooled is below the dew point, liquid will precipitate from the gas. This liquid is desirably recycled continuously to the fluidized bed. It is possible to recycle the precipitated liquid to the bed as liquid droplets carried in the recycle gas stream, as described, for example, in EP-A-89691, U.S. Pat. No. 4,543,399, WO 94/25495 and U.S. Pat. No. 5,352,749, which are hereby incorporated by reference. A particularly preferred method of recycling the liquid to the bed is to separate the liquid from the recycle gas stream and to reinject this liquid directly into the bed, preferably using a method which generates fine droplets of the liquid within the bed. This type of process is described in WO 94/28032, the teachings of which are also hereby incorporated by reference.

The polymerization reaction occurring in the gas fluidized bed is catalyzed by the continuous or semi-continuous addition of catalyst. The catalyst can also be subjected to a prepolymerization step, for example, by polymerizing a small quantity of olefin monomer in a liquid inert diluent, to provide a catalyst composite comprising catalyst particles embedded in olefin polymer particles.

The polymer is produced directly in the fluidized bed by catalyzed (co)polymerization of the monomer(s) on the fluidized particles of catalyst, supported catalyst or prepolymer within the bed. Start-up of the polymerization reaction is achieved using a bed of preformed polymer particles, which, preferably, is similar to the target polyolefin, and conditioning the bed by drying with inert gas or nitrogen prior to introducing the catalyst, the monomer(s) and any other gases which it is desired to have in the recycle gas stream, such as a diluent gas, hydrogen chain transfer agent, or an inert condensable gas when operating in gas phase condensing mode. The produced polymer is discharged continuously or discontinuously from the fluidized bed as desired, optionally exposed to a catalyst kill and optionally pelletized.

Similarly, supported catalysts for use in slurry polymerization may be prepared and used according to previously known techniques. Generally such catalysts are prepared by the same techniques as are employed for making supported catalysts used in gas phase polymerizations. Slurry polymerization conditions generally encompass polymerization of a $C_{2-20}$ olefin, diolefin, cycloolefin, or mixture thereof in an aliphatic solvent at a temperature below that at which the polymer is readily soluble in the presence of a supported catalyst.

It is understood that the present invention is operable in the absence of any component which has not been specifically disclosed. The following examples are provided in order to further illustrate the invention and are not to be construed as limiting. Unless stated to the contrary, all parts and percentages are expressed on a weight basis. Where stated the term "room temperature" refers to a temperature from 20 to 25° C., the term "overnight" refers to a time from 12 to 18 hours, and the term "mixed alkanes" refers to the aliphatic solvent, Isopar® E, available from Exxon Chemicals Inc.

EXAMPLES

Tris(perfluorophenyl)borane (FAB) was obtained as a solid from Boulder Scientific Inc. and used without further purification. Trimethylaluminum (TMA) in toluene or hexanes, and triisobutylaluminum (TIBA) were purchased from Aldrich Chemical Co. Tris(perfluorophenyl)aluminum (FAAL, as a toluene adduct) was prepared by exchange reaction between tris(perfluorophenyl)borane and trimethylaluminum as disclosed in U.S. Pat. No. 5,602,269. All solvents were purified using the technique disclosed by Pangborn et al, *Organometallics*, 1996, 15, 1518–1520. All compounds and solutions were handled under an inert atmosphere (dry box). All chemical shift for $^{19}F$ NMR spectra were relative to a fixed external standard ($CFCl_3$) in benzene $d_6$ or toluene $d_8$, both of which were dried over N/K alloy and filtered prior to use. $^1H$ and $^{13}C$ NMR shifts were referenced to internal solvent resonances and are reported relative to TMS.

Example 1

In a glove box, FAAL (0.125 g, 0.20 mmol, toluene adduct) was dissolved in 20 mL of dry toluene in a flask and TMA (0.101 mL, 2.0 M in toluene, 0.20 mmol) was added dropwise. The reaction mixture was stirred for 10 min at room temperature and an NMR spectra of an aliquot taken from the mixture indicated the exchange reaction was complete. The solvent was then removed under reduced pressure and the residue was dried in vacuo to afford 0.11 g of $(C_6F_5)_3Al_2Me_3$ (FAAL•TMA) as a white crystalline solid (91 percent yield). This dimeric adduct complex, $(C_6F_5)_3Al_2Me_3$, is stable in solution at room temperature under an inert atmosphere. An NMR spectra showed no noticeable changes after standing at room temperature for 24 h.

$^1H$ NMR ($C_7D_8$, 23° C.) shows only a broad singlet for Me resonance at δ 0.01 ppm.

$^{19}F$ NMR ($C_7D_8$, 23° C.) shows only one type of $C_6F_5$ resonance at δ −122.26 (dd, 2 F, o-F), −151.38 (s, br, 1 F, p-F), −160.73 (t, 2 F, m-F).

$^{13}C$ NMR ($C_7D_8$): δ 7.25 (Me), 151.40 (d), 148.54 (t), 144.00 (s), 140.65 (s), 138.97 (d), 135.42 (d) ($C_6F_5$). Peaks become sharp at 80° C. and all data are consistent with the dynamic features of this complex.

Single crystals suitable for X-ray diffraction studies were obtained from a slow cooling of a hexane solution of the above dinuclear species at −35° C. over 4 days. The resulting ORTEP drawing generated from single crystal X-ray analysis of the compound is illustrated in FIG. 1.

Example 2

In a glove box, FAB (0.250 g, 0.49 mmol) was dissolved in 20 mL of dry toluene in a flask and TMA (0.488 mL, 2.0 M in toluene, 0.98 mmol) was added dropwise. The reaction mixture was stirred for 2 h at room temperature and the solvent was removed under reduced pressure. The residue was then dried in vacuo to afford 0.24 g of $(C_6F_5)_3Al_2Me_3$ (FAAL•TMA) as a white solid (82 percent yield). The $^1H$ and $^{19}F$ NMR spectra of the product are consistent with the dimeric structure of $(C_6F_5)_3Al_2Me_3$ and are essentially identical to those described in Example 1.

Example 3

In a glove box, FAB (0.512 g, 1.00 mmol) was dissolved in 50 mL of dry hexane in a flask and TMA (0.75 mL, 2.0 M in toluene, 1.50 mmol) was added dropwise. The reaction mixture was stirred for 2 h at room temperature and the solvent was removed under reduced pressure. The residue was then dried in vacuo to afford $(C_6F_5)_4Al_2Me_2$ (FAAL•0.5TMA) as a white solid (quantitative yield).

$^1H$ NMR ($C_6D_6$, 23° C.) shows only a broad singlet for Me resonance at δ −0.01 ppm and $^{19}F$ NMR ($C_6D_6$, 23° C.) shows only broad peaks for one type of $C_6F_5$ resonance at δ −122.29–123.04 (br, 2 F, o-F), −150.84 (br, 1 F, p-F), −160.67 (br, 2 F, m-F). Peaks become sharp at 80° C. and all data are consistent with the dynamic features of this complex.

Example 4

In a glove box, FAB (0.077 g, 0.15 mmol) was dissolved in 10 mL of dry hexane in a flask and TMA (0.09 mL, 2.0 M in toluene, 0.18 mmol) was added dropwise. The reaction mixture was stirred for 2 h at room temperature and the solvent was removed under reduced pressure. The residue was then dried in vacuo to afford 0.07 g of $(C_6F_5)_5Al_2Me$ (FAAL•0.2TMA) as a white solid (86 percent yield).

$^1H$ NMR ($C_6D_6$, 23° C.) shows only a broad singlet for Me resonance at much downfield-shifted region of δ 0.15 ppm as compared with TMA (−0.36 ppm) and $^{19}F$ NMR ($C_6D_6$, 23° C.) shows only broad peaks for one type of $C_6F_5$ resonance at δ −122.30 (br, 2 F, o-F), −150.50 (br, 1 F, p-F), −160.45 (br, 2 F, m-F). All data are consistent with the dynamic features of this complex.

Example 5

In a glove box, FAAL (9.92 mg, 0.016 mmol, toluene adduct) was dissolved in 0.7 mL of toluene-$d_8$ in a J-Young NMR tube and TMA (0.016 mL, 2.0 M in toluene, 0.032 mmol) was added dropwise. NMR spectra were recorded after mixing these reagents in the NMR tube for 15 min. $^1$H NMR ($C_7D_8$, 23° C.) for $(C_6F_5)_2Al_2Me_4$ (FAAL•2TMA) shows only a broad singlet for Me resonance at δ −0.08 and $^{19}$F NMR ($C_7D_8$, 23° C.) shows only one type of $C_6F_5$ resonance at δ −122.15 (dd, 2 F, o-F), −151.7 (s, br, 1 F, p-F), −160.88 (t, 2 F, m-F). All data are consistent with the dynamic features of this dimeric adduct.

Example 6

In a glove box, FAAL (9.92 mg, 0.016 mmol, toluene adduct) was dissolved in 0.7 mL of toluene-$d_8$ in a J-Young NMR tube and TMA (0.08 mL, 2.0 M in toluene, 0.16 mmol) was added dropwise. NMR spectra were recorded after mixing these reagents in the NMR tube for 15 min. $^1$H NMR ($C_7D_8$, 23° C.) for $(C_6F_5)Al_2Me_5$ (FAAL•5TMA) shows only a broad singlet for Me resonance at δ −0.22 and $^{19}$F NMR ($C_7D_8$, 23° C.) shows only one type of $C_6F_5$ resonance at δ −122.20 (dd, 2 F, o-F), −152.34 (t, 1 F, p-F), −161.10 (t, 2 F, m-F). All data are consistent with the dynamic features of this dimeric adduct.

Example 7

In a glove box, FAB (0.25 g, 0.49 mmol) was dissolved in 25 mL of dry hexane in a glass flask and triisobutylaluminum (TIBA) (0.194 g, 0.98 mmol) was added dropwise. The reaction mixture was stirred at room temperature and the reaction was monitored by $^{19}$F NMR analysis of aliquots taken from the reaction mixture. The exchange reaction was essentially complete within 2 h. $^{19}$F NMR analysis at 60° C. indicated the product is one compound, $(C_6F_5)_3Al_2(iBu)_3$, but at room temperature, broadened peaks appeared, indicating dynamic exchange takes place in solution.

$^{19}$F NMR (60° C.) for $(C_6F_5)_3Al_2(iBu)_3$: δ −120.60 (d, 2 F, o-F), −147.71 (t, 1 F, p-F), −157.08 (t, 2 F, m-F).

Example 8

In a glove box, FAAL (0.02 mmol) and TIBA (0.01 mmol) were mixed in 0.7 mL of $C_6D_6$ in an J-Young NMR tube. The tube contents were stirred at room temperature for 15 minutes and the NMR spectra recorded. Both $^1$H NMR and $^{19}$F NMR analysis indicated the formation of $(C_6F_5)_2Al(iBu)$, which at variable temperatures exhibits the monomer-dimer dynamic features.

$^1$H NMR ($C_6D_6$, 23° C.): δ 1.89 (overlapping with structure from dimer, 1 H, Me$_2$CHCH$_2$—), 0.99 (d, $J_{H-H}$=6.6 Hz, 6 H, Me$_2$CHCH$_2$—), 0.55 (s, br, 2 H, Me$_2$CHCH$_2$—). $^{19}$F NMR ($C_6D_6$, 23° C.): δ −121.74 (d, $^3J_{F-F}$=18.3 Hz, 2 F, o-F), −151.45 (t, $^3J_{F-F}$=20.9 Hz, 1 F, p-F), −161.20 (tt, $^3J_{F-F}$=24.5 Hz, 2 F, m-F).

POLYMERIZATIONS

A 2-liter Parr reactor was used in the polymerizations. All feeds were passed through columns of alumina and a decontaminant (Q-5™ catalyst available from Englehardt Chemicals Inc.) prior to introduction into the reactor. Catalyst and cocatalysts are handled in a glovebox containing an atmosphere of argon or nitrogen.

A stirred 2.0 liter reactor is charged with about 740 g of Isopar-E™ mixed alkanes solvent (available from Exxon Chemicals Inc.) and 118 g of 1-octene comonomer. Hydrogen is added as a molecular weight control agent by differential pressure expansion from a 75 ml addition tank at 25 psi (2070 kPa). The reactor is heated to the polymerization temperature of 130° C. and saturated with ethylene at 500 psig (3.4 MPa). Catalyst ((t-butylamido) (tetramethylcyclopentadienyl)-dimethylsilanetitanium 1,3-pentadiene) (obtained from Boulder Scientific Inc.) and cocatalyst, as dilute solutions in toluene, were mixed and transferred to a catalyst addition tank and injected into the reactor. The polymerization conditions are maintained for 15 minutes with ethylene added on demand. The resulting solution is removed from the reactor, quenched with isopropyl alcohol, and stabilized by addition of 10 ml of a toluene solution containing approximately 67 mg of a hindered phenol antioxidant (Irganox™ 1010 from Ciba Geigy Corporation) and 133 mg of a phosphorus stabilizer (Irgafos 168 from Ciba Geigy Corporation).

Between polymerization runs a wash cycle in which 850 g of mixed alkanes is added to the reactor and the reactor heated to 150° C. The reactor is emptied of the heated solvent immediately before beginning a new polymerization run.

Polymers are recovered by drying in a vacuum oven set at 140° C. for about 20 hours. Density values are derived by determining the polymers mass when in air and when immersed in methylethyl ketone. Micro melt index values (MMI) are obtained using a Custom Scientific Instrument Inc. Model CS-127MF-015 apparatus at 190° C. MMI (micro-melt index) are unit-less values calculated as follows: MMI=1/(0.00343 t −0.00251), where t=time in seconds. Results are contained in Table 1.

TABLE 1

| Run | Activator | catalyst/ activator* | Exotherm (° C.) | Yield (g) | Eff. (g × 10$^6$/gTi) | Density g/ml | MMI |
| --- | --- | --- | --- | --- | --- | --- | --- |
| CE | B-(C$_6$F$_5$)$_3$ | 1.5/1.5 | 3.5 | 32.2 | 0.45 | 0.901 | 3.8 |
| CE | B-(C$_6$F$_5$)$_3$ | 1.5/1.5 | 1.3 | 48.7 | 0.68 | 0.901 | 3.9 |
|  | Example 1 | 1/3 | 1.6 | 13.0 | 0.27 | 0.901 | 0.4 |
|  | Example 3 | 1/4 | 1.2 | 32.1 | 0.67 | 0.899 | 0.7 |
|  | Example 4 | 1/4 | 1.9 | 30.4 | 0.63 | 0.902 | 0.6 |

CE: comparative example, not an example of the invention
*μmoles of each based on metal or metalloid Example 9

3.01 g of silica supported methylalumoxane containing approximately 33 mole percent trimethylaluminum (based on total aluminum) (Witco 02794/HL/04) was slurried in 25 mL toluene. To this slurry was added 0.511 g [B(C$_6$F$_5$)$_3$] as a dry solid. The mixture was agitated for 3 days. At this time, the solids were collected on a fritted funnel, washed three times with 15 mL portions of toluene and once with 20 mL pentane, and dried in vacuo. A 2.00 g portion of the modified supported material was slurried in 18 mL pentane, and 1.0 mL of a 0.1 M solution of (tetramethylcyclopentadienyl) dimethylsilyl(N-tert-butylamido) titanium (II) (1,3-pentadiene) in pentane was added. After 5 minutes, the solids were collected on a fritted funnel, washed twice with 10 mL pentane, and dried in vacuo to yield the supported catalyst product as a pale green solid.

POLYMERIZATION

A 1 gallon computer-controlled stirred autoclave was charged with approximately 1450 g of mixed alkanes solvent and about 125 g of 1-octene. 10 mmoles of $H_2$ was added as a molecular weight control agent. The mixture was stirred and heated to 130° C. The solution was saturated with ethylene at 450 psig (3.4 MPa). Catalyst solutions were prepared by combining solutions of [(tetramethylcyclopentadienyl) dimethylsilyl-N-tert-butylamido] titanium (II) (1,3-pentadiene) (0.005 M in mixed alkanes), and the supported cocatalyst of the invention. The catalyst/cocatalyst composition was dispesed in mixed hydrocarbons and the mixture was added to the reactor via a pump. The reactor temperature was controlled by controlling the temperature of the reactor jacket. After 10 minutes polymerization time, the resulting solution was removed from the reactor into a nitrogen-purged collection vessel. After cooling, the vessel was removed to the air and a solution of an antioxidant/stabilizer was added and the polymer was dried.

Under the foregoing polymerization conditions 0.1 g of the above supported catalyst gave approximately 200 g of ethylene/octene copolymer for a catalyst efficiency of 3.1 Kg polymer/gTi). A comparative polymerization using the same metal complex and Witco 02794/HL/04 supported MAO (without treatment with $[B(C_6F_5)_3]$) under substantially identical polymerization conditions showed a catalyst efficiency of 1.5 Kg polymer/gTi.

What is claimed is:

1. A compound corresponding to the formula: $Ar^f{}_5Al_2Q^1$, where;

$Q^1$ independently each occurrence is selected from $C_{1-20}$ alkyl; and $Ar^f$ is a fluorinated aromatic hydrocarbyl moiety of from 6 to 30 carbon atoms.

2. A compound according to claim 1 wherein $Ar^f$ each occurrence is perfluoroaryl and $Q^1$ each occurrence is $C_{1-4}$ alkyl.

3. A compound according to claim 1 wherein $Ar^f$ each occurrence is perfluorophenyl and $Q^1$ each occurrence is methyl.

4. A process for preparing a compound corresponding to the formula:

$Ar^f{}_zAl_2Q^1{}_{6-z}$ where;

$Q^1$ independently each occurrence is selected from $C_{1-20}$ alkyl;

$Ar^f$ is a fluorinated aromatic hydrocarbyl moiety of from 6 to 30 carbon atoms;

z is a number greater than 0 and less than 6, and the moiety: $Ar^f{}_zAl_2Q^1{}_{6-z}$ is an adduct of tri (fluoroarylaluminum) with from a sub-stoichiometric to a super-stoichiometric amount of a trialkylaluminum having from 1 to 20 carbons in each alkyl group, said process comprising contacting:
   A) a compound of the formula $Ar^f{}_3Al$, with
   B) a compound of the formula $AlQ^1{}_3$,
   wherein $Ar^f$, and $Q^1$ are as previously defined, in a molar ratio A:B from 1:0.1 to 1:10 and at a temperature from −50 to 200° C.

5. A process for preparing a compound corresponding to the formula:

$Ar^f{}_zAl_2Q^1{}_{6-z}$ where;

$Q^1$ independently each occurrence is selected from $C_{1-20}$ alkyl;

$Ar^f$ is a fluorinated aromatic hydrocarbyl moiety of from 6 to 30 carbon atoms;

z is a number greater than 0 and less than 6, and the moiety: $Ar^f{}_zAl_2Q^1{}_{6-z}$ is an adduct of tri (fluoroarylaluminum) with from a sub-stoichiometric to a super-stoichiometric amount of a trialkylaluminum having from 1 to 20 carbons in each alkyl group, said process comprising contacting:
   A) a compound of the formula $Ar^f{}_3B$, with
   B) a compound of the formula $AlQ^1{}_3$,
   wherein $Ar^f$, and $Q^1$ are as previously defined, in a molar ratio A:B from 1:1.1 to 1:10 and at a temperature from 20 to 60° C.

6. A catalyst composition for polymerization of addition polymerizable monomers comprising, in combination, a Group 3–10 metal complex containing a delocalized π-bonded ligand group that is capable of being activated to polymerize addition polymerizable compounds, and a compound according to claim 1, or the reaction product thereof.

7. A polymerization process comprising contacting one or more addition polymerizable monomers under polymerization conditions with a catalyst composition according to claim 6.

8. A polymerization process according to claim 7 which is a solution polymerization.

9. A polymerization process according to claim 8 which is a continuous solution polymerization.

10. A polymerization process according to claim 7 which is a gas phase, powder bed or slurry polymerization.

11. A polymerization process according to claim 10 wherein the catalyst composition additionally comprises a support.

12. A catalyst composition according to claim 6 wherein the metal complex corresponds to the formula: $L_lMX_mX'_nX''_p$, or a dimer thereof wherein:

L is an anionic, delocalized, π-bonded group that is bound to M, containing up to 50 nonhydrogen atoms, optionally two L groups may be joined together through one or more substituents thereby forming a bridged structure, and further optionally one L may be bound to X through one or more substituents of L;

M is a metal of Group 4 of the Periodic Table of the Elements in the +2, +3 or +4 formal oxidation state;

X is an optional, divalent substituent of up to 50 non-hydrogen atoms that together with L forms a metallocycle with M;

X' is an optional neutral Lewis base having up to 20 non-hydrogen atoms;

X" each occurrence is a monovalent, anionic moiety having up to 40 non-hydrogen atoms, optionally, two X" groups may be covalently bound together forming a divalent dianionic moiety having both valences bound to M, or form a neutral, conjugated or non-conjugated diene that is π-bonded to M (whereupon M is in the +2 oxidation state), or further optionally one or more X" and one or more X' groups may be bonded together thereby forming a moiety that is both covalently bound to M and coordinated thereto by means of Lewis base functionality;

l is 1 or 2;

m is 0 or 1;

n is a number from 0 to 3;

p is an integer from 0 to 3; and the sum, l+m+p, is equal to the formal oxidation state of M.

13. A catalyst composition for polymerization of addition polymerizable monomers comprising, in combination, a Group 3–10 metal complex containing a delocalized π-bonded ligand group that is capable of being activated to polymerize addition polymerizable compounds and a compound prepared according to the process of claim 4, or the reaction product thereof.

14. A catalyst composition according to claim 13 wherein the metal complex corresponds to the formula: $L_lMX_mX'_nX''_p$, or a dimer thereof wherein:

L is an anionic, delocalized, π-bonded group that is bound to M, containing up to 50 nonhydrogen atoms, optionally two L groups may be joined together through one or more substituents thereby forming a bridged structure, and further optionally one L may be bound to X through one or more substituents of L;

M is a metal of Group 4 of the Periodic Table of the Elements in the +2, +3 or +4 formal oxidation state;

X is an optional, divalent substituent of up to 50 non-hydrogen atoms that together with L forms a metallocycle with M;

X' is an optional neutral Lewis base having up to 20 non-hydrogen atoms;

X" each occurrence is a monovalent, anionic moiety having up to 40 non-hydrogen atoms, optionally, two X" groups may be covalently bound together forming a divalent dianionic moiety having both valences bound to M, or form a neutral, conjugated or non-conjugated diene that is π-bonded to M (whereupon M is in the +2 oxidation state), or further optionally one or more X" and one or more X' groups may be bonded together thereby forming a moiety that is both covalently bound to M and coordinated thereto by means of Lewis base functionality;

l is 1 or 2;

m is 0 or 1;

n is a number from 0 to 3;

p is an integer from 0 to 3; and the sum, l+m+p, is equal to the formal oxidation state of M.

15. A polymerization process comprising contacting one or more addition polymerizable monomers under polymerization conditions with a catalyst composition according to claim 13.

16. A polymerization process according to claim 15 which is a solution polymerization.

17. A polymerization process according to claim 16 which is a continuous solution polymerization.

18. A polymerization process according to claim 15 which is a gas phase, powder bed or slurry polymerization.

19. A polymerization process according to claim 18 wherein the catalyst composition additionally comprises a support.

* * * * *